(12) United States Patent
Oh et al.

(10) Patent No.: US 8,009,291 B2
(45) Date of Patent: Aug. 30, 2011

(54) SENSOR FOR MEASURING LIVING BODY INFORMATION AND KEYPAD ASSEMBLY USING THE SAME

(75) Inventors: Jung-Taek Oh, Yongin-si (KR); Dong-Kyoon Han, Seongnam-si (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 606 days.

(21) Appl. No.: 12/182,190

(22) Filed: Jul. 30, 2008

(65) Prior Publication Data
US 2009/0033937 A1 Feb. 5, 2009

(30) Foreign Application Priority Data
Jul. 31, 2007 (KR) .......................... 10-2007-0076992

(51) Int. Cl.
*G01J 4/00* (2006.01)

(52) U.S. Cl. ....................................................... 356/366
(58) Field of Classification Search ................... 356/366
See application file for complete search history.

(56) References Cited

U.S. PATENT DOCUMENTS

| | | | | |
|---|---|---|---|---|
| 5,596,987 A | * | 1/1997 | Chance | 600/310 |
| 6,975,898 B2 | * | 12/2005 | Seibel | 600/473 |

* cited by examiner

*Primary Examiner* — Roy Punnoose
(74) *Attorney, Agent, or Firm* — Cha & Reiter, LLC (57) ABSTRACT

A sensor for measuring living body information and a keypad assembly including the sensor includes a light guide panel for guiding a first light. A light extracting pattern is provided on the light guide panel for outputting the first light guided by the light guide panel to an exterior of the light guide panel. A light coupling pattern is provided on the light guide panel for changing a proceeding direction of a second light incident from the exterior of the light guide panel, so that the second light is guided by the light guide panel.

20 Claims, 5 Drawing Sheets

SENSOR FOR MEASURING LIVING BODY INFORMATION AND KEYPAD ASSEMBLY USING THE SAME

CLAIM OF PRIORITY

This application claims the benefit under 35 U.S.C. §119 (a) from a Korean Patent Application filed in the Korean Intellectual Property Office on Jul. 31, 2007 and assigned Serial No. 2007-76992, the disclosure of which is incorporated herein by reference in its entirety.

BACKGROUND OF THE INVENTION

1. Field of the Invention

The present invention relates generally to a sensor for measuring physical factors associated with a living body, such as bio-information or chemical information. More particularly, the present invention relates to a light guide panel for measuring living body information such as the pulse rate and a sensor using the same.

2. Description of the Related Art

The pulse rate is a basic figure used for measuring the stresses in living bodies, permitting a more accurate assessment of the state of exercises, the quantity of exercises, and the condition of the living body, etc.

Conventionally, an electrocardiogram (ECG) sensor is normally used for measuring the pulse rate by detecting an ECG signal using a multipolar electrode. In addition, a photo sensor has been recently proposed in conjunction with irradiating a light on the skin surface of a living body using a Light Emitting Diode (LED), and the photo sensor detects light that is output from the skin surface due to scattering in the living body. Through the use of a photodiode, the living body information can be measured.

Recently, intensive research is being conducted on a portable terminal with a sensor for measuring living body information. However, the aforementioned ECG sensor and photo sensor need a separate space for their installation, impeding the slimness of the portable terminal. Further, the ECG sensor and photo sensor need to contact the skin surface, significantly restricting design on the external appearance of the portable terminal.

Therefore, there is a demand for a sensor for measuring living body information, which can be readily integrated together with other elements in the portable terminal, and can also be mounted in the portable terminal without being exposed to the exterior.

SUMMARY OF THE INVENTION

The present invention provides a sensor for measuring living body information, which can be readily integrated together with other elements in a portable terminal and can also be mounted in the portable terminal without being exposed to the exterior, and a keypad assembly having the same.

According to an exemplary aspect of the present invention, there is provided a sensor for measuring information of a living body. The sensor includes a light guide panel for guiding a first light; a light extracting pattern provided on the light guide panel, for outputting the first light guided by the light guide panel to an exterior of the light guide panel; and a light coupling pattern provided on the light guide panel, for changing a proceeding direction of a second light incident from the exterior of the light guide panel so that the second light is guided by the light guide panel.

According to another exemplary aspect of the present invention, there is provided a keypad assembly that may include a key sheet having at least one key top; a sensor including a first light guide panel for guiding a first light, a first light extracting pattern for outputting the first light toward the key sheet, and a light coupling pattern for changing a proceeding direction of a second light incident from the key sheet so that the second light is guided by the first light guide panel; a second light guide panel including a second light extracting pattern for guiding a third light and outputting the third light toward the key sheet; and a switch board including at least one switch.

BRIEF DESCRIPTION OF THE DRAWINGS

The above and other exemplary aspects, features and advantages of the present invention will become more apparent from the following detailed description when taken in conjunction with the accompanying drawings in which.

DETAILED DESCRIPTION

Exemplary embodiments of the present invention will now be described in detail with reference to the annexed drawings. The drawings have been provided for illustrative purposes, and the claimed invention is not limited to the examples shown and described herein. In the following description, a detailed description of known functions and configurations incorporated herein has been omitted for clarity and conciseness.

Figure 1:
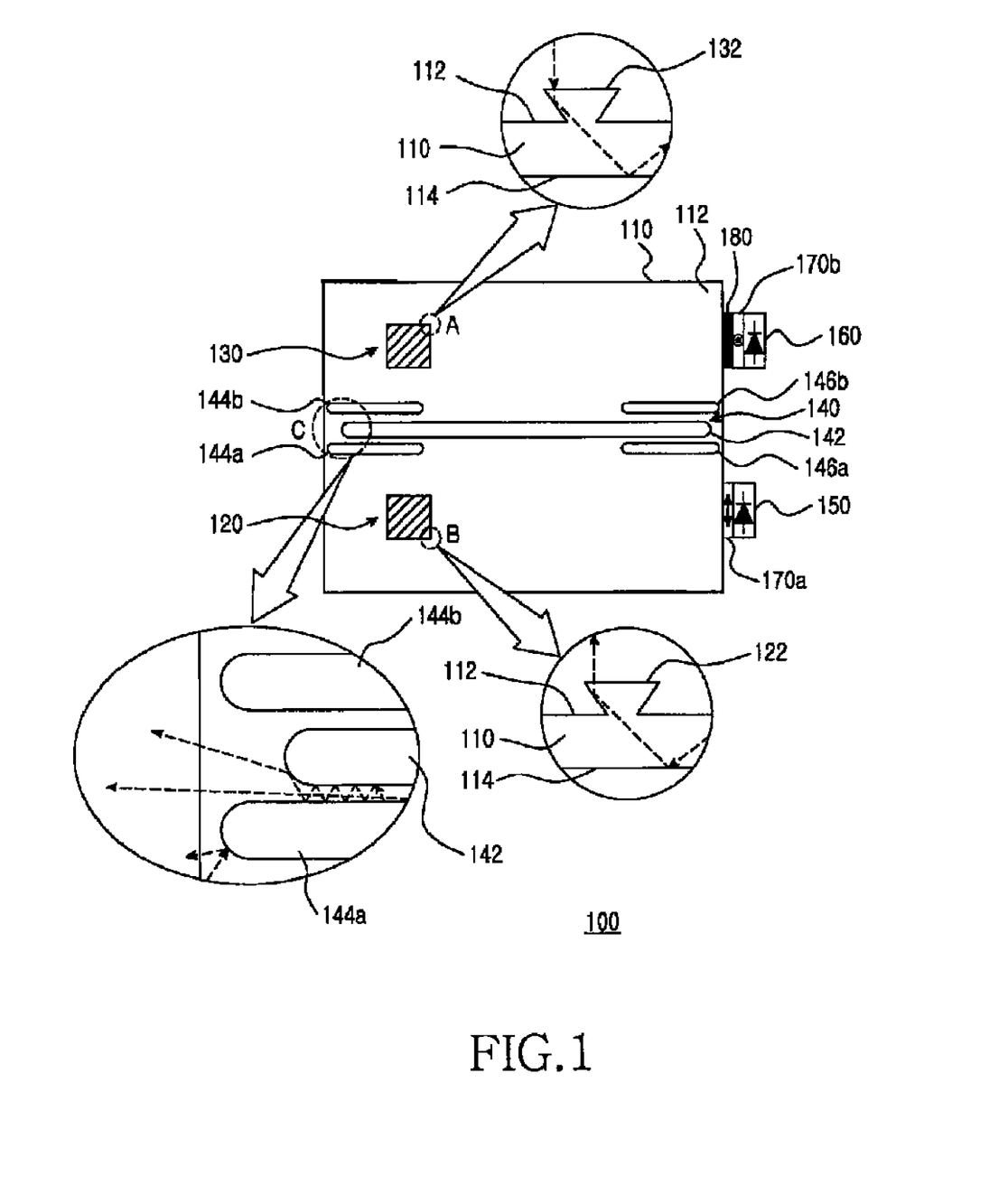
FIG. 1 is a plan view illustrating a sensor for measuring living body information according to a exemplary embodiment of the present invention.

FIG. 1 is a plan view illustrating a sensor for measuring living body information according to an exemplary embodiment of the present invention.

A sensor 100 may include a first light guide panel 110 for guiding a light, a first light source 150 for generating a light, a photodetector 160 for photoelectric conversion, first and second polariscopes 170a and 170b for polarization, and a bandpass filter 180. The phrase 'guiding a light' as used herein typically means that the light proceeds through the total internal reflection between a top surface 112 and a bottom surface 114 of the first light guide panel 110.

The first light source 150 may output a first light having a Near Infra-Red (NIR) wavelength, and for example, the wavelength can be, for example, about 940 nm. An LED may be used as the first light source 150.

Generally, the first light guide panel 110 may have a shape of a flat board, and includes a top surface 112, the bottom surface 114, and four side surfaces. The first light coupled to the interior of the first light guide panel 110 is guided from a first side surface of the first light guide panel 110 to a second side surface situated in the opposite side thereof through the total internal reflection between the top surface 112 and the bottom surface 114. In this example, the first side surface of the first light guide panel 110 faces a light emitting surface of the first light source 150, and the first light output from the first light source 150 is coupled to the interior of the first light guide panel 110 through the first side surface. The first light guide panel 110, as it has an elasticity (in other words, self-restoring force), is restored to its original shape after being transformed by the external pressure. The first light guide panel 110 can be formed of materials having characteristics such as low hardness, high elastic strain, high elastic restoring force, and high light transmittance, and is preferably formed of materials including but in no way limited to polycarbonate, acrylic resin, polyurethane, polymethylmethacrylate (PMMA), and silicone.

Still referring to FIG. 1, the first light guide panel 110 includes a first light extracting pattern 120, a light coupling pattern 130, and a light blocking member 140.

The first light extracting pattern 120 is formed on the top (upper) surface 112 of the first light guide panel 110, and outputs the first light guided by the first light guide panel 110 to the exterior of the first light guide panel 110. The first light output to the exterior of the first light guide panel 110 is incident upon the skin surface of a living body. The first light extracting pattern 120 is composed of a plurality of protrusions 132 each having an exemplary shape of a reversed quadrangular pyramid, and the first light incident upon each of the protrusions 132 is radiated out to the exterior through the top surface of the protrusion 132 after being reflected from the side surface of the protrusion 132. Since the first light incident upon the top surface of the protrusion 132 cannot satisfy the total reflection condition, it penetrates the top surface of the protrusion 132 (when its incidence angle is less than a critical angle).

The first light extracting pattern 120 can have an arbitrary shape and structure for outputting the first light guided by the first light guide panel 110 to the exterior of the first light guide panel 110, and such light extraction can be realized by deflecting reflection, refraction, or scattering. The term 'deflecting reflection' as used herein typically refers to the phenomenon where an incident angle and a reflection angle for the light incident upon the bottom surface 114 of the first light guide panel 110 are different from each other.

For example, each element of the first light extracting pattern 120 may comprise a polymer layer formed by groove, protrusion, scratch, and printing.

Figure 2A:
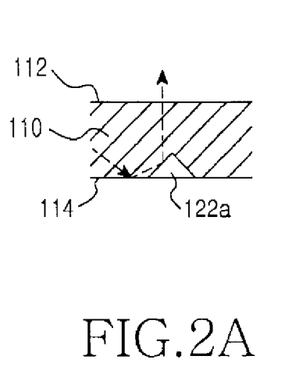
FIGS. 2A to 2C are diagrams illustrating various shapes of a first light extracting pattern.
Figure 2B:
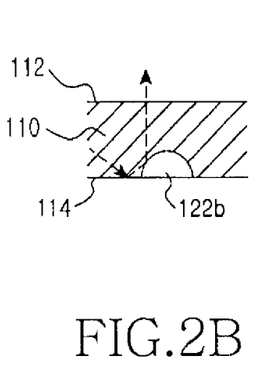
Figure 2C:
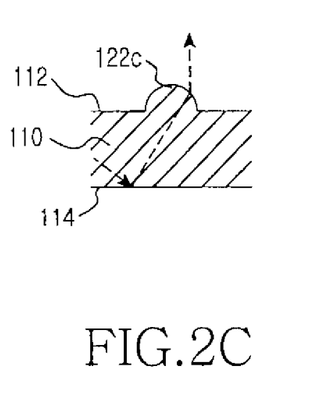

FIGS. 2A to 2C are diagrams illustrating examples of various shapes of a first light extracting pattern. Shown in FIGS. 2A to 2C are exemplary elements constituting a first light extracting pattern, and the first light extracting pattern can be composed of a plurality of elements.

FIG. 2A shows a V-groove 122*a* (groove whose transaction being perpendicular to its longitudinal direction has a 'V'-shape) formed on the bottom surface 114 of the first light guide panel 110 by depressed-carving, and the first light incident upon the V-groove 122*a* is reflected from an inclined plane of the V-groove 122*a*, and then output to the exterior through the top surface 112 of the first light guide panel 110.

FIG. 2B shows an example of a hemispherical groove 122*b* formed on the bottom surface 114 of the first light guide panel 110 by depressed-carving, and the first light incident upon the hemispherical groove 122*b* is reflected from the surface of the hemispherical groove 122*b*, and then output to the exterior through the top surface 112 of the first light guide panel 110.

FIG. 2C shows an example of a hemispherical protrusion 122*c* formed on the top surface 112 of the first light guide panel 110 by embossed-carving, and the first light incident upon the hemispherical protrusion 122*c* is output to the exterior during refraction by the hemispherical protrusion 122*c*.

Although the groove and protrusion have a hemispherical shape as illustrated in FIGS. 2B and 2C, the groove and protrusion can have various shapes, including but not limited to a triangular pyramid and quadrangular pyramid shape.

The light coupling pattern 130, which is formed on the top surface 112 of the first light guide panel 110, and changes a proceeding direction of a second light incident from the exterior of the first light guide panel 110 so that it is guided by the first light guide panel 110. The 'second light' indicates a light output from the skin surface of the living body due to scattering in the living body, among the first lights irradiated on the living body. The light coupling pattern 130 is composed of a plurality of protrusions 132 each having a shape of a reversed quadrangular pyramid, and the second light incident upon each of the protrusions 132 penetrates the top surface of the protrusion 132 to be incident upon a side surface of the protrusion 132, and the second light reflected from the side surface of the protrusion 132 is guided by the first light guide panel 110. The light coupling pattern and light extracting pattern may be arranged along a same surface of the light guide panel, with a predetermined distance therebetween.

The light coupling pattern 130 can have an arbitrary shape and structure for changing a proceeding direction of the second light incident from the exterior of the first light guide panel 110 so that it is guided by the first light guide panel 110, and such light coupling can be realized by deflecting reflection, refraction, or scattering.

For example, each element of the light coupling pattern 130 may be a groove, a protrusion, or a scratch.

Figure 3A:
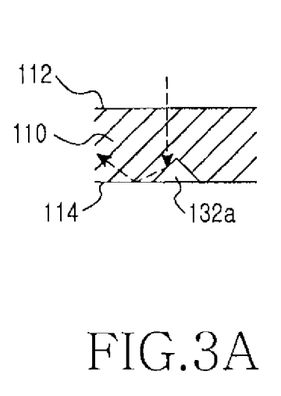
FIGS. 3A to 3C are diagrams illustrating various shapes of a light coupling pattern.
Figure 3B:
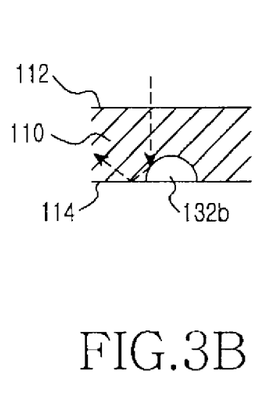
Figure 3C:
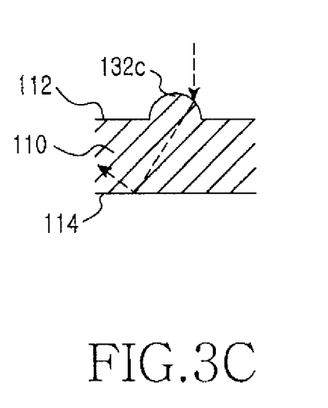

FIGS. 3A to 3C are diagrams illustrating various shapes of a light coupling pattern. Shown in FIGS. 3A to 3C are exemplary elements constituting the light coupling pattern, and the light coupling pattern can be composed of a plurality of elements.

FIG. 3A shows an example of a V-groove 132*a* (groove whose transaction being perpendicular to its longitudinal direction has a 'V'-shape) formed on the bottom surface 114 of the first light guide panel 110 by depressed-carving. The second light penetrating the top surface 112 of the first light guide panel 110 is incident upon the V-groove 132*a*, and the second light reflected from one inclined plane of the V-groove 132*a* is guided by the first light guide panel 110.

FIG. 3B shows an example of a hemispherical groove 132*b* formed on the bottom surface 114 of the first light guide panel 110 by depressed-carving. The second light penetrating the top surface 112 of the first light guide panel 110 is incident upon the groove 132*b*, and the second light reflected from the surface of the groove 132*b* is guided by the first light guide panel 110.

FIG. 3C shows an example of a hemispherical protrusion 132*c* formed on the top surface 112 of the first light guide panel 110 by embossed-carving. The second light incident upon the protrusion 132*c* is coupled to the interior of the first light guide panel 110 as it is refracted by the protrusion 132*c*, and the second light coupled to the interior of the first light guide panel 110 is guided by the first light guide panel 110.

Now referring back to FIG. 1, the light blocking member 140 is situated between the first light extracting pattern 120 and the light coupling pattern 130, and blocks a light incident from any one side so that it may not proceed to the other side passing through the light blocking member 140. The sensor 100 has a structure divided into a light output unit and a light input unit by the light blocking member 140. The light blocking member 140 is extended long in a longitudinal direction (the shortest-length moving direction reaching from the first side surface to the second side surface) of the first light guide panel 110, and includes at least one hole passing through the first light guide panel 110 in a thickness direction (the shortest-length moving direction reaching from the top surface 112 to the bottom surface 114).

In the exemplary embodiment shown in FIG. 1, the light blocking member 140 includes a first hole 142 having the longest length; second and third holes 144a and 144b are disposed in both sides of one end of the first hole 142, so as to be adjacent to each other; and fourth and fifth holes 146a and 146b disposed in both sides of another end of the first hole 142 so as to be adjacent to each other. The second and third holes 144a and 144b are situated closer to the second side surface compared with the first hole 142, and the fourth and fifth holes 146a and 146b are situated closer to the first side surface compared with the first hole 142. Both ends of each hold have a round shaped so that the light reflected at each of the ends is output to the exterior passing through side surfaces of the first light guide panel 110.

Optionally, a reflection layer having a high reflectance (e.g., about 90~100%) can be stacked on a corresponding inner surface of the first light guide panel 110, which defines each of the holes.

The photodetector 160 shown in FIG. 1 is disposed such that its light receiving surface faces the first side surface of the first light guide panel 110, and converts the second light incident upon the first side surface of the first light guide panel 110 through penetration, into an electrical signal. A photodiode can be used as the photodetector 160.

A controller (not shown) receives the electrical signal from the photodetector 160, and detects a pulse rate of the living body from the periodic power change of the electrical signal. For example, the controller can be a microprocessor commonly included in a portable radio terminal.

The bandpass filter 180 may be disposed between the first side surface of the first light guide panel 110 and the light receiving surface of the photodetector 160, and serves to prevent the surrounding light (lighting, natural light, etc.) from being input to the photodetector 160. The bandpass filter 180 passes the second light, and blocks the remaining noise lights. For example, the bandpass filter 180 has an exemplary pass wavelength band of about 940±5 nm.

The first and second polariscopes 170a and 170b serve to prevent the first light output from the first light source 150 from being directly input to the photodetector 160, and the first polariscope 170a is disposed between the first side surface of the first light guide panel 110 and the light emitting surface of the first light source 150, and the second polariscope 170b is disposed between the first side surface of the first light guide panel 110 and the light receiving surface of the photodetector 160. A first polarization axis of the first polariscope 170a and a second polarization axis of the second polariscope 170b are substantially perpendicular to each other. The first light output from the first light source 150 is polarized along the first polarization axis as it passes through the first polariscope 170a. If the polarized first light is incident upon the second polariscope 170b, since a polarization direction of the first light and the second polarization axis of the second polariscope 170b are perpendicular to each other, the first light is blocked by the second polariscope 170b.

Figure 4:
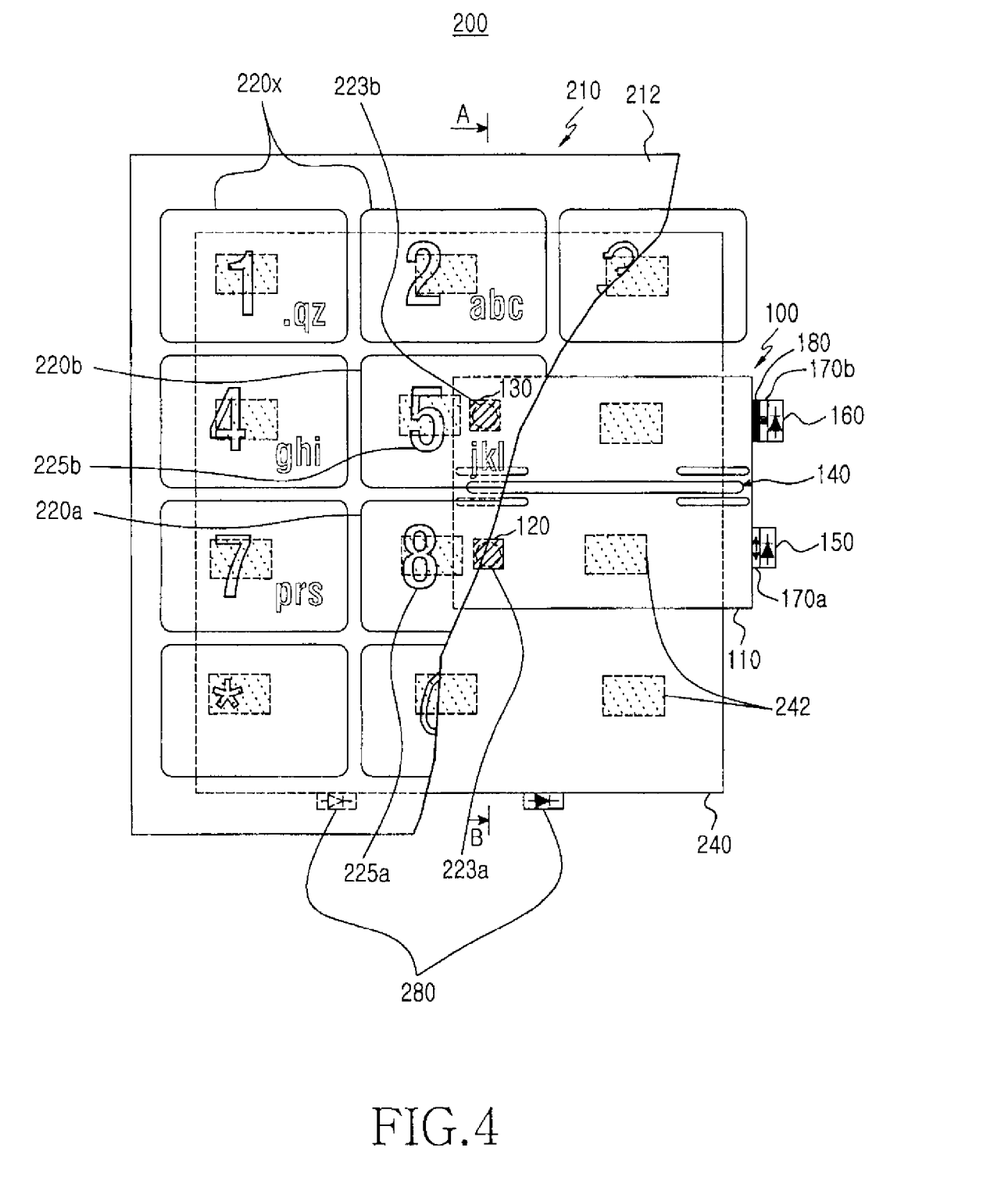
FIG. 4 is a plan view illustrating an example of a partially cut-open keypad assembly with a sensor for measuring living body information.
Figure 5:
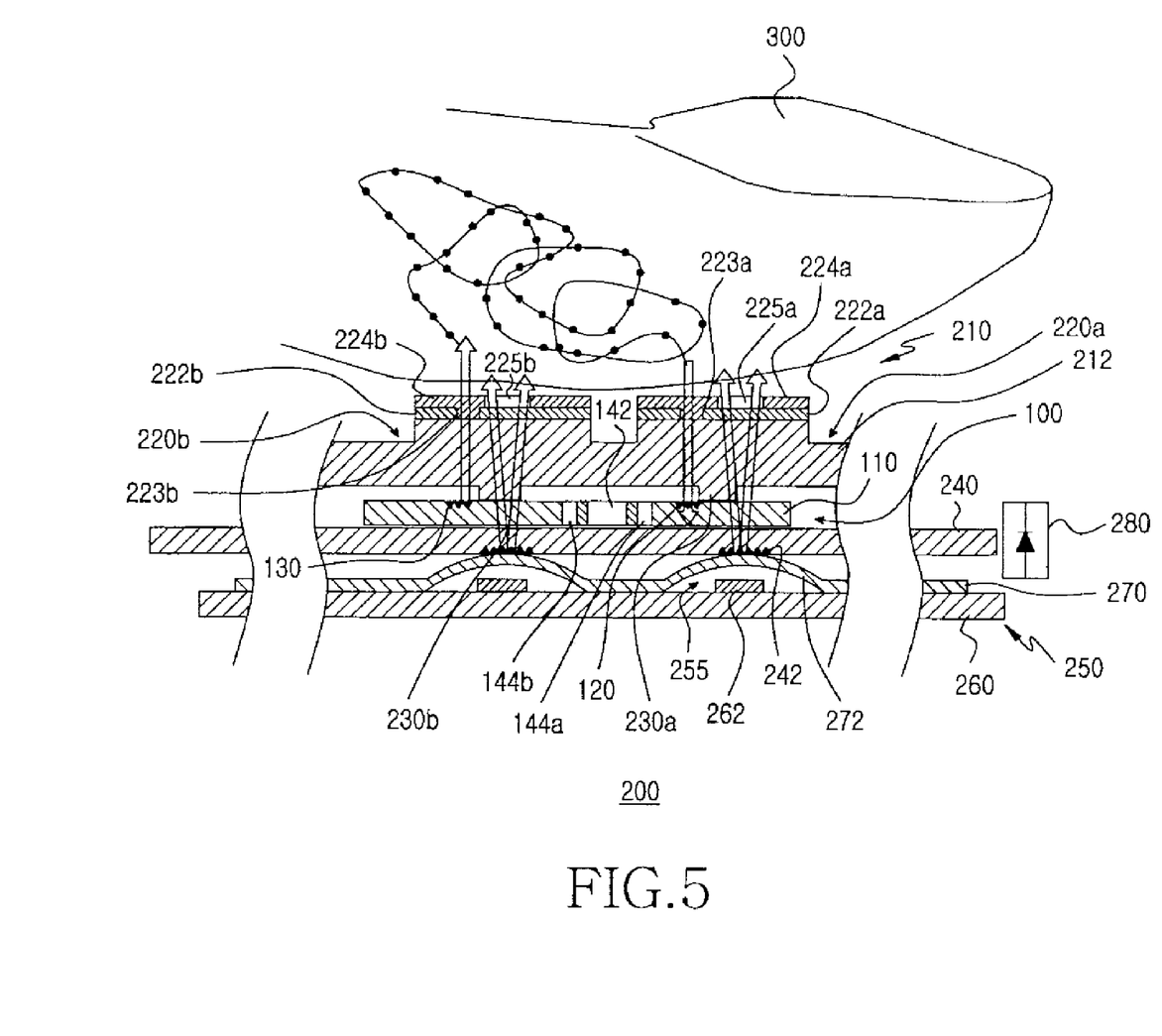
FIG. 5 is a cross-sectional view illustrating the keypad assembly, taken along a line A-B of FIG. 4.

FIG. 4 is a plan view illustrating an example of a partially cut-open keypad assembly with a sensor for measuring living body information, and FIG. 5 is a cross-sectional view illustrating the keypad assembly, taken along a ling A-B. For example, the keypad assembly 200 can be mounted in a portable radio terminal. The keypad assembly 200 includes a switch board 250, a second light guide panel 240, at least one second light source 280, a sensor 100 for measuring the living body information measure, and a key sheet 210.

The key sheet 210 includes an elastic pad 212, a plurality of key tops 220a, 220b and 220x, and a plurality of protrusions 230a and 230b (best shown in FIG. 5).

The elastic pad 212 in this example preferably has a shape of a rectangular board, and the elastic pad 212, as it has an elasticity, is adapted to return to its original position after any of the key tops 220a, 220b and 220x are pressed by the user. That is, the elastic pad 212 has a self-restoring force, and is restored to its original shape after being transformed to restore the key tops 220a, 220b and 220x to their original positions after operation of the key tops 220a, 220b and 220x. In order to prevent a light leakage phenomenon, the top surface of the elastic pad 212 where the key tops 220a, 220b and 220x are not disposed can be covered by, for example, a housing (included in the portable radio terminal). Alternatively, to prevent the light leakage phenomenon, the top surface portion of the elastic pad 212 where the key tops 220a, 220b and 220x are not disposed can be subject to black ink printing.

Still referring to FIG. 4, the multiple key tops 220a, 220b and 220x are disposed on the top surface of the elastic pad 212, and the key tops 220a, 220b and 220x each can be adhered to the top surface of the elastic pad 212 using adhesive, or can be formed with the elastic pad 212 into one body through injection molding. The key tops 220a, 220b and 220x each can be formed of the same material as the elastic pad 212, or can be formed of another material, such as polycarbonate or acrylic resin. Although the key tops 220a, 220b and 220x each have a shape of a rectangular block in this embodiment, they can also have an arbitrary shape such as cylinder, cylindroid, etc.

Referring now to FIG. 5, first and second opaque layer (222a and 224a), (222b and 224b) are stacked on the respective top surfaces of two key tops 220a and 220b (hereinafter, first and second key tops) situated in the center of the key sheet 210 among the key tops 220a, 220b and 220x, and second opaque layers are stacked on the top surfaces of the remaining key tops 220x. The first opaque layer (222a, 222b) is opaque to the NIR light, and the second opaque layer (224a, 224b) is opaque to the visible light. The first opaque layer (222a, 222b) has a first opening (223a, 223b) for passing the NIR light therethrough, and the second opaque layer (224a, 224b) has at least one second opening (225a, 225b) for passing the visible light therethrough.

For example, first and second opaque layers (222a and 224a), (222b and 224b) can be formed through the ink printing process.

Figure 6A:
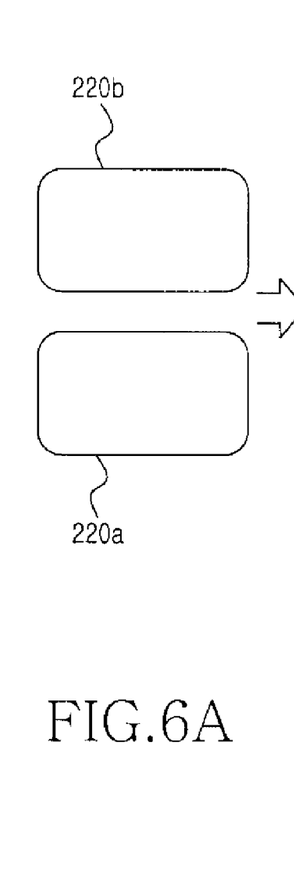
FIGS. 6A to 6C are diagrams illustrating a process of forming first and second opaque layers through an ink printing process.
Figure 6B:
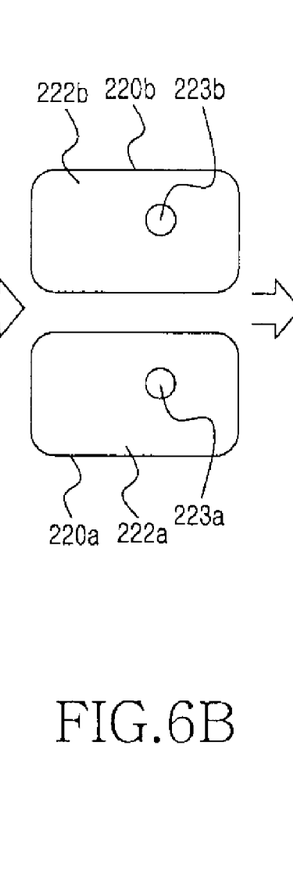
Figure 6C:
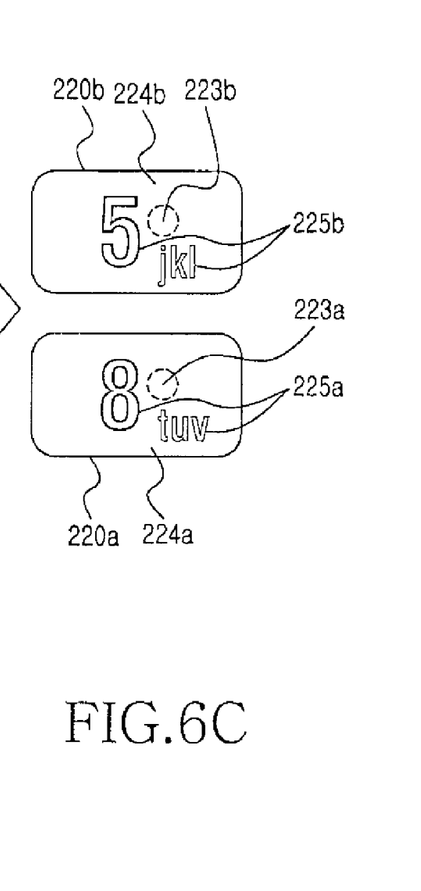

FIGS. 6A to 6C are diagrams illustrating a process of forming first and second opaque layers through an ink printing process.

Referring to FIG. 6A, a first opaque layer (222a, 222b) having a circular first opening (223a, 223b) is stacked on the top surface of each of the first and second key tops 220a and 220b through the ink printing process. The first opaque layer (222a, 222b), as it has a high absorbance for a wavelength of about 800 nm or longer, has a characteristic that it is opaque to the NIR light. For example, when NIR paint made of tris ammonium is used as paint for printing the first opaque layer (222a, 222b), it can absorb a light (with a wavelength of about 940 nm) of the light source for pulse measurement, and its surrounding NIR light. For example, Epolight™ 2063 Near Infrared Dye made by Epolin company can be used as the NIR paint.

The first light source 150 (shown in FIG. 1) outputs a first light having a NIR wavelength, and for example, the wavelength can be about 940 nm. LED can be used as the first light source 150.

Referring to FIG. 6B, a second opaque layer (224a, 224b) with a second opening (225a, 225b) having a shape of character, number, symbol, etc. is stacked on the first opaque layer (222a, 222b) through an ink printing process. The second opaque layer (224a, 224b), as it has a high absorbance for a wavelength of about 800 nm or shorter, has a characteristic that it is opaque to the visible light. For example, when paint made of a specific organic dye mixture is used as paint for printing the second opaque layer (224a, 224b), it can absorb a light having a wavelength of 800 nm or shorter, and pass the NIR light therethrough. For example, Epolight™ 7527 Visible Opaque Dye made by Epolin company can be used as the NIR paint.

The multiple protrusions 230a and 230b (shown in FIG. 5) are disposed on the bottom surface of the elastic pad 212. The protrusions 230a and 230b can be formed of the same or different material as/from the elastic pad 212 in a united fashion, or can be adhered to the bottom surface of the elastic pad 212 after being formed separately. Each protrusion (230a, 230b) can have an arbitrary shape such as, for example, cone, trapezoidal hexahedron, etc. The protrusion (230a, 230b) is aligned with the corresponding key top (220a, 220b) in a thickness direction of the keypad assembly 200.

Now referring to FIG. 5, the sensor 100 intervenes between the key sheet 210 and the second light guide panel 240, and the first light extracting pattern 120 is aligned with the first opening 223a of the first key top 220a in a thickness direction of the keypad assembly 200, and the light coupling pattern 130 is aligned with the first opening 223b of the second key top 220b in a thickness direction of the keypad assembly 200. The first light output from the sensor 100 is radiated to the exterior of the keypad assembly 200 through the first opening 223a of the first key top 220a, and then is incident upon the skin surface of a living body 300. The light (i.e., second light) output from the skin surface of the living body 300 due to scattering in the living body 300, among the first lights irradiated on the living body 300, is input to the sensor 100 through the first opening 223b of the second key top 220b.

The second light source 280 is disposed such that its light emitting surface faces the first side surface of the second light guide panel 240, and outputs a third light having a visible light wavelength. While there can be various different types light sources in the present invention, one such example is an LED that can be used as the second light source 280. Note that one of the second light sources 280 in FIG. 5 and the other light source 280 is not visible as it is out of the viewed angle.

Still referring to FIG. 5, the second light guide panel 240 may have the general a shape of, for example, a rectangular flat board having a top surface, bottom surface and four side surfaces. The third light coupled to the interior of the second light guide panel 240 is guided from a first side surface of the second light guide panel 240 to a second side surface situated in the opposite side thereof through the total internal reflection between the top surface and the bottom surface. In this particular case, the first side surface of the second light guide panel 240 faces the light emitting surface of the second light source 280, and the third light output from the second light source 280 is coupled to the interior of the second light guide panel 240 through the first side surface. The second light guide panel 240, as it has an elasticity (in other words, self-restoring force), is restored to its original shape after being distorted by the user. The second light guide panel 240 can be formed of materials having one or more attributes including low hardness, high elastic strain, high elastic restoring force, and high light transmittance, and is preferably formed of materials such as, for examples polycarbonate, acrylic resin, polyurethane, PMMA, silicone, etc.

The second light guide panel 240 has a plurality of second light extracting patterns 242, and the second light extracting patterns 242 each output the third light guided by the second light guide panel 240 to the exterior of the second light guide panel 240, thereby lighting up the corresponding key top (220a, 220b). The second light extracting patterns 242 are each aligned with the corresponding key top (220a, 220b) in a thickness direction of the keypad assembly 200. Alternatively, the second light extracting patterns 242 can be formed on the top surface of the second light guide panel 240.

The second light extracting patterns 242 each can be realized with at least one V-groove formed on the bottom surface of the second light guide panel 240. When each of the second light extracting patterns 242 is realized with the V-groove, the V-groove can be extended from one side surface of the second light guide panel 240 through the other side surface situated in the opposite side thereof.

Also, the second light extracting patterns 242 can each be realized with grooves in various shapes, formed on the bottom surface or the top surface of the second light guide panel 240 by depressed-carving, or with a plurality of protrusions formed thereon by embossed-carving. The grooves or protrusions can have various shapes such as hemisphere, triangular pyramid, etc. Alternatively, the second light extracting patterns 242 each can be a polymer layer formed by scratching, printing, etching, etc.

When the second light extracting patterns 242 are formed on the bottom surface of the second light guide panel 240 as illustrated, the second light extracting patterns 242 each deflecting-reflect at least a part of the third light incident thereupon toward the corresponding key top (220a, 220b). The term 'deflecting reflection' (and the variation "deflecting-reflect" as used herein generally refers to the phenomenon where an incidence angle and a reflection angle for the light incident upon the bottom surface of the second light guide panel 240 are different from each other, and such deflecting reflection can be mirror reflection or scattering (diffuse reflection). Also, the second light extracting patterns 242 each can be formed on the top surface of the second light guide panel 240, and in this particular case, the second light extracting patterns 242 each penetrate at least a part of the third light incident thereupon toward the corresponding key top (220a, 220b). Since a part of the third light reflected toward the corresponding key top (220a, 220b) by each of the second light extracting patterns 242 cannot satisfy the total reflection condition (when the incidence angle is less than the critical angle), it is output to the exterior after penetrating the top surface of the second light guide panel 240. In addition, the third light passing through the second light extracting patterns 242 without being reflected by the each of the second light extracting patterns 242, and a part of the third light reflected by the second light extracting patterns 242 continuously proceed into the second light guide panel 240, satisfying the total reflection condition, thereby contributing to lighting up other key tops.

As the third light in the second light guide panel 240 is attenuated while proceeding from the first side surface adjacent to the second light source 280 to the second side surface, it may show an aspect in which luminance distribution occurring at the top of the key sheet 210 decreases little by little as it goes from the first side surface of the second light guide panel 240 to the second side surface thereof. In order to cope with such non-uniformity of luminance, it is possible to allow a density of the second light extracting pattern 242 to increase little by little as it goes from the first side surface of the second light guide panel 240 to the second side surface thereof, on the basis of the same total pattern size. In this case, the density change of the second light extracting pattern 242 can be realized by changing the number of its constituent elements or by changing a size of each constituent element, and the density of the second light extracting pattern 242 can be defined as an area occupied by the constituent elements of the second light extracting pattern 242 per unit area.

Still referring to FIG. 5, the switch board 250 includes a printed circuit board 260, and a dome sheet 270. The printed circuit board 260 includes a plurality of conductive contact members 262 formed on its top surface, and the contact members 262 each constitute a switch 255 together with a corresponding dome 272. Each switch 255 is aligned with the corresponding key top 220a (220b), the protrusion 230a (230b) and the second light extracting patterns 242 in a thickness direction of the keypad assembly 200.

The dome sheet 270 is adhered or attached to the top surface of the printed circuit board 260, and has a plurality of conductive domes 272 having a hemispherical shape, and the domes 272 fully cover their corresponding contact members 262.

For example, if the user presses the first key top 220a, as a portion of the key sheet 210 situated under the first key top 220a is transformed toward the switch board 250, a corresponding protrusion 230a belonging to the transformed portion presses the corresponding dome 272, with the sensor 100 and the second light guide panel 240 intervening therebetween. The pressed dome 272 makes an electrical contact with the corresponding contact members 262 (resulting in 'switch-on'). A preset key signal is generated by the electrical contact.

While the invention has been shown and described with reference to a certain preferred embodiment thereof, it will be understood by those skilled in the art that various changes in form and details may be made therein without departing from the spirit and scope of the invention as defined by the appended claims.

For example, an exemplary embodiment of the present invention has shown that the first light extracting pattern and the light coupling pattern have the same structure, and each can function reversibly (i.e., can simultaneously perform the light extraction function and the light coupling function), and also has shown that it is possible to operate the first light source and the photodetector without mutual interference therebetween, using the first and second polariscopes. Therefore, the present invention, though its measurement accuracy may decrease, can remove the light coupling pattern and the light blocking member from the structure shown in FIG. 1, and use the first light extracting pattern as a light extracting/ light coupling pattern.

Although the protrusions are formed herein on the bottom surface of the key sheet, the protrusions can also be formed on the bottom surface of the second light guide panel. In this case, the second light extracting pattern can be formed on the bottom surfaces of the protrusions, or can be formed on both the bottom surfaces of the protrusions and the surroundings of the protrusions. Alternatively, the second light extracting pattern can be formed on the bottom surface of the second light guide panel, and then, the protrusions can be adhered thereunder.

Since the proposed sensor for measuring living body information and keypad assembly using the same has a structure based on light guide panels, it can be readily mounted in the portable terminal, and is not exposed to the exterior, thus ensuring easy exterior design and making it possible to simply measure various physiological factors such as the pulse rate and its associated stresses with the simple structure.

What is claimed is:

1. A sensor for measuring living body information, the sensor comprising:
   a light guide panel for guiding a first light;
   a light extracting pattern arranged on the light guide panel, for outputting the first light guided by the light guide panel to an exterior of the light guide panel; and
   a light coupling pattern arranged on the light guide panel, for changing a proceeding direction of a second light incident from the exterior of the light guide panel so that the second light is guided by the light guide panel.

2. The sensor of claim 1, wherein the light extracting pattern and light coupling pattern are arranged adjacently along a same surface of the light guide panel.

3. The sensor of claim 2, wherein the same surface comprises a top surface of the light guide panel, and the light extracting pattern and light coupling pattern have a predetermined distance therebetween.

4. The sensor of claim 1, wherein the second light incident from the exterior of the light guide panel comprises light scattered off a skin surface of a living body.

5. The sensor of claim 1, further comprising;
   a light source for generating the first light; and
   a photodetector for converting the second light into an electrical signal.

6. The sensor of claim 1, further comprising:
   a light blocking member which is situated between the light extracting pattern and the light coupling pattern, and blocks a light incident thereupon.

7. The sensor of claim 6, wherein the light blocking member includes at least one hole passing through the light guide panel in a direction from the top surface to a bottom surface of the light guide panel.

8. The sensor of claim 5, further comprising:
   a first polariscope disposed between the light guide panel and the light source; and
   a second polariscope disposed between the light guide panel and the photodetector;
   wherein polarization axes of the first and second polariscopes cross each other.

9. The sensor of claim 5, further comprising:
   a bandpass filter, disposed between the light guide panel and the photodetector, for passing the second light and blocking a remaining noise lights.

10. The sensor of claim 8, wherein the polarization axes of the first polariscope and second polariscope are substantially perpendicular; and
    wherein the light guide panel includes a top surface having a groove arranged such that the second light penetrating the top surface of the light guide panel is incident upon the groove.

11. The sensor of claim 8, wherein the polarization axes of the first polariscope and second polariscope are substantially perpendicular; and
    wherein the light guide panel includes a surface having a protrusion arranged such that the second light incident upon the protrusion is coupled to an interior of the first light panel as the second light is being refracted by the protrusion.

12. A keypad assembly comprising:
    a key sheet including at least one key top;
    a sensor including a first light guide panel for guiding a first light, a first light extracting pattern for outputting the first light toward the key sheet, and a light coupling pattern for changing a proceeding direction of a second light incident from the key sheet so that the second light is guided by the first light guide panel;

a second light guide panel including a second light extracting pattern for guiding a third light and outputting the third light toward the key sheet; and a switch board including at least one switch.

13. The keypad assembly of claim 12, wherein the sensor further comprises:

a first light source for generating the first light; and a photodetector for converting the second light into an electrical signal.

14. The keypad assembly of claim 12, wherein the sensor further comprises:

a light blocking member, disposed between the first light extracting pattern and the light coupling pattern, for blocking a light incident thereupon.

15. The keypad assembly of claim 14, wherein the light blocking member includes at least one hole passing through the first light guide panel in a direction from a top surface to a bottom surface of the light guide panel.

16. The keypad assembly of claim 13, wherein the sensor further comprises:

a first polariscope disposed between the first light guide panel and the first light source; and a second polariscope disposed between the first light guide panel and the photodetector;

wherein polarization axes of the first and second polariscopes cross each other.

17. The keypad assembly of claim 16, wherein the polarization axes of the first and second polariscopes are substantially perpendicular.

18. The keypad assembly of claim 13, wherein the sensor further comprises:

a bandpass filter, disposed between the first light guide panel and the photodetector, for passing the second light and blocking a remaining noise lights.

19. The keypad assembly of claim 13, wherein the key sheet includes a first key top aligned with the first light extracting pattern, and a second key top aligned with the light coupling pattern, wherein a first opaque layer being opaque to the first and second lights and a second opaque layer being opaque to the third light are stacked on a top surface of each of the key tops.

20. The keypad assembly of claim 19, wherein the first opaque layer includes a first opening for passing the first or second light therethrough, and the second opaque layer includes a second opening for passing the third light therethrough.

* * * * *